United States Patent
Pennig

[11] Patent Number: 5,609,595
[45] Date of Patent: Mar. 11, 1997

[54] FIXATION PIN FOR SMALL-BONE FRAGMENTS

[76] Inventor: Dietmar Pennig, Hans-Driesch-Strasse 12, 50935 Koln, Germany

[21] Appl. No.: 392,386

[22] Filed: Feb. 22, 1995

Related U.S. Application Data

[63] Continuation-in-part of Ser. No. 214,365, Mar. 16, 1994, Pat. No. 5,433,719.

[30] Foreign Application Priority Data

Mar. 25, 1993 [DE] Germany .................. 43 09 707.3

[51] Int. Cl.⁶ ...................................... A61B 17/56
[52] U.S. Cl. ...................... 606/73; 606/72; 606/65; 606/104
[58] Field of Search ........................ 606/72, 73, 69, 606/70, 71, 65, 104; 128/898; 411/401, 411, 424, 368, 155, 156, 544, 542, 426

[56] References Cited

U.S. PATENT DOCUMENTS

| | | |
|---|---|---|
| 1,105,105 | 7/1914 | Sherman . |
| 2,760,488 | 8/1956 | Pierce ................................. 606/73 |
| 3,057,221 | 9/1962 | Lanius, Jr. . |
| 4,059,102 | 11/1977 | Devas . |
| 4,524,765 | 6/1985 | Zbikowski . |
| 4,549,538 | 10/1985 | Schadrack, III et al. ............. 606/104 |
| 4,662,365 | 5/1987 | Gotzen . |
| 4,791,918 | 9/1988 | Von Hasselbach ................. 606/69 |
| 5,019,078 | 5/1991 | Perren et al. . |
| 5,062,843 | 11/1991 | Mahony, III ......................... 606/73 |
| 5,196,016 | 3/1993 | Buser et al. . |
| 5,259,398 | 11/1993 | Vrespa . |

FOREIGN PATENT DOCUMENTS

| | | |
|---|---|---|
| 0369266 | 10/1990 | European Pat. Off. . |
| 0424734 | 5/1991 | European Pat. Off. . |
| 2499400 | 8/1982 | France . |
| 2649310 | 1/1991 | France . |
| 3244819 | 12/1982 | Germany . |
| 0314021 | 5/1989 | Germany . |
| WO9308758 | 5/1993 | WIPO . |

*Primary Examiner*—Michael Powell Buiz
*Assistant Examiner*—Mark S. Leonardo
*Attorney, Agent, or Firm*—Hopgood, Calimafde, Kalil & Judlowe

[57] ABSTRACT

The invention contemplates a compression wire for fixated retention of a fractured small bone fragment in an osteosynthesis procedure. The wire comprises a smooth-walled shank portion and an adjoining threaded portion, of lesser diameter than the diameter of the shank portion, there being a step-down shoulder between the shank portion and the threaded portion. The shank portion is adapted for chucked engagement to a portable rotary drill, and the distal end of the threaded portion is configured for self-tapping entry into and threaded implantation in bone. The implantation is complete when the shoulder engages cortex tissue of the fragment, holding the same in compression against remainder structure of the fractured bone. Once implanted, the shank may be nipped by a cutter tool at relatively close offset from the shoulder.

10 Claims, 3 Drawing Sheets

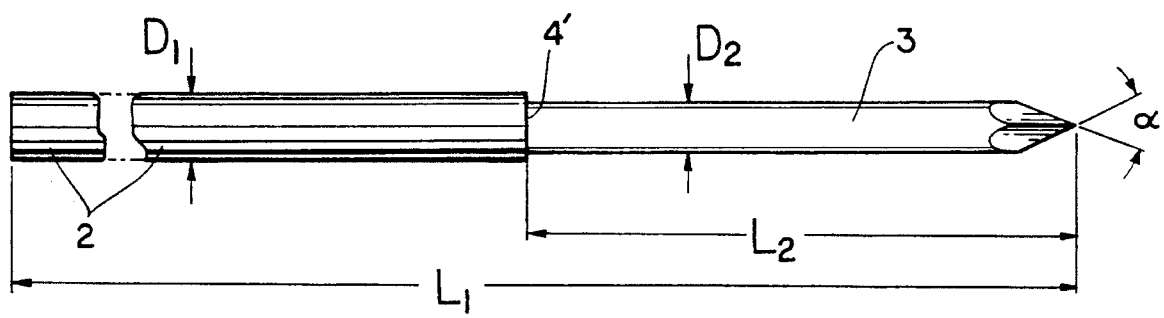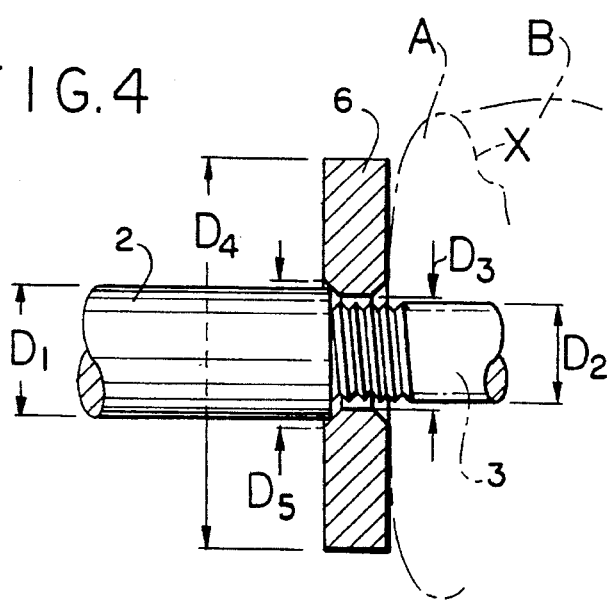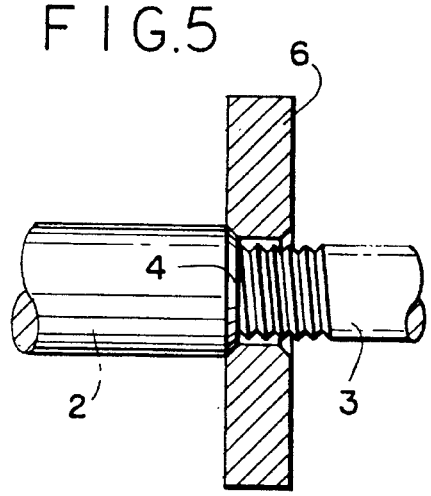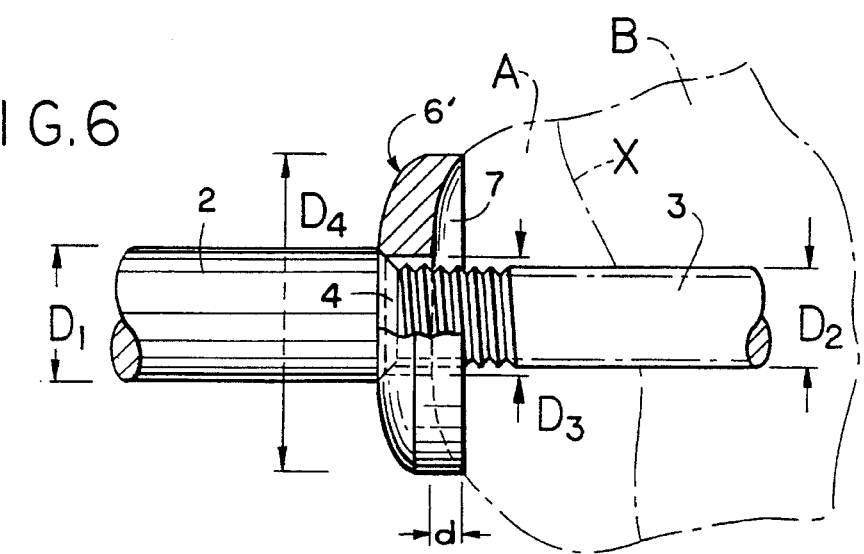

5,609,595

FIXATION PIN FOR SMALL-BONE FRAGMENTS

RELATED CASE

This application is a continuation-in-part of application Ser. No. 08/214,365, filed Mar. 16, 1994 (now U.S. Pat. No. 5,433,719).

BACKGROUND OF THE INVENTION

The present invention relates to a fixation pin for use in retaining small-bone fragments in an osteosynthesis procedure.

It is generally known in osteosyntheses to fix bone fragments by screws or pins. In the case of small-bone splinterings, the screws or pins available in the prior art are, however, much too large to fix a small splintered portion of a given bone to another portion of the same bone without damaging these parts. The fixing of such small bone fragments by means of simple pins or nails is therefore problematical, since there is no abutment to hold the parts together, and the bone may shift on the outer wall of the pin or nail.

More specifically, the use of Kirschner wires (K-wires) in small-bone and bone-fragment fixation dates back to the early part of this century and is a common procedure in orthopedics, offering advantages of simplicity of use, and low cost. Threaded K-wires, designed to produce better anchorage in bone, were a later modification. And small-fragment screws, using the lag-screw principle were in wide use in the 1970's, to provide rigid fixation of small fragments. However, all of these techniques had their disadvantages.

K-wires offer poor purchase; a fragment can slide with respect to a wire. Any bending of a wire, as for securing purposes, may result in displacement or fracture of a fragment. And wire migration into a joint through the skin carries the risk of infection.

Threaded K-wires have only a small distal threaded portion, which can improve anchorage to the main or larger bone fragment to which a smaller fragment is to be re-united; but most of the disadvantages of the K-wire remain.

Use of the lag-screw technique involves a more complex procedure; two drill sizes are required for pre-drilling, and there must be a pretapping of bone. This technique is not suitable for small bone fragments, and there is risk of bone contamination.

BRIEF STATEMENT OF THE INVENTION

The object of the present invention is to provide a fixation pin for bone fragments which, despite its necessarily small size, will produce a dependable fixation of a small-bone fragment to the adjacent remainder of the bone from which the fragment developed.

Another object is to achieve the above object in a single motor-driven operation which assures prolonged retention of the fixation.

The invention achieves this object by providing a small-bone pin or wire with an elongate smooth-walled shank. The distal end portion of the pin has a step-down transition to a smaller-diameter threaded portion, with a sharp distal point for self-tapping entry into bone. The step-down transition provides a shoulder which may be radial but is preferably conical and which can abut a bone fragment or splinter, while the threaded portion is anchored to the main part of the same bone.

Stated in other words, a small-bone pin of the invention has a smooth-walled shank portion along a relatively large part of the overall length of the pin, and a relatively short threaded part with a sharp bone-cutting distal tip extends beyond the shank portion. In use of this pin, the shank is chucked to a portable drill, and the threaded portion is driven into the bone fragment and into the remainder or main fraction of the same bone; exposed cortex of the bone fragment is abutted by the shoulder or conical step formed between the threaded portion and the shank portion, so that the fragment is fixed to the remainder of the original bone with a degree of compression best judged by the surgeon, and it is no longer possible for the bone fragment to slide on the pin.

When relying solely upon the small-bone pin of the invention, the shank portion may be located within surrounding muscular tissue. The shank portion also projects externally, for easy chuck access and for later cut-off to desired length, using a suitable tool; in that event, it is appropriate to refer to the bone pin of the invention as a compression wire. The expression "compression wire" is therefore in frequent use in this specification.

Optionally, and depending upon the shape or condition of the proximal face of the bone fragment to be secured, a special washer is applicable over the threaded portion of the pin (a) with a counterbore adapted to locate against the shoulder, (b) with a larger diameter than that of the shank portion of the pin, and (c) with a distal face adapted for relatively large-area retaining engagement with the bone fragment.

DETAILED DESCRIPTION OF THE DRAWINGS

Preferred embodiments of the invention will be described in conjunction with the accompanying drawings, in which:

FIG. 3 is a view in longitudinal elevation of a modified small-bone pin or compression wire;

FIG. 4 is an enlarged fragmentary view of coacting elements of the invention in an installed condition, pursuant to an optional employment of kit components of the invention;

FIG. 5 is a view similar to FIG. 4, for a further modification;

FIG. 6 is another enlarged fragmentary view of coacting elements of the invention in an installed condition, pursuant to a further optional employment of kit components of the invention;

DETAILED DESCRIPTION

Figure 1:
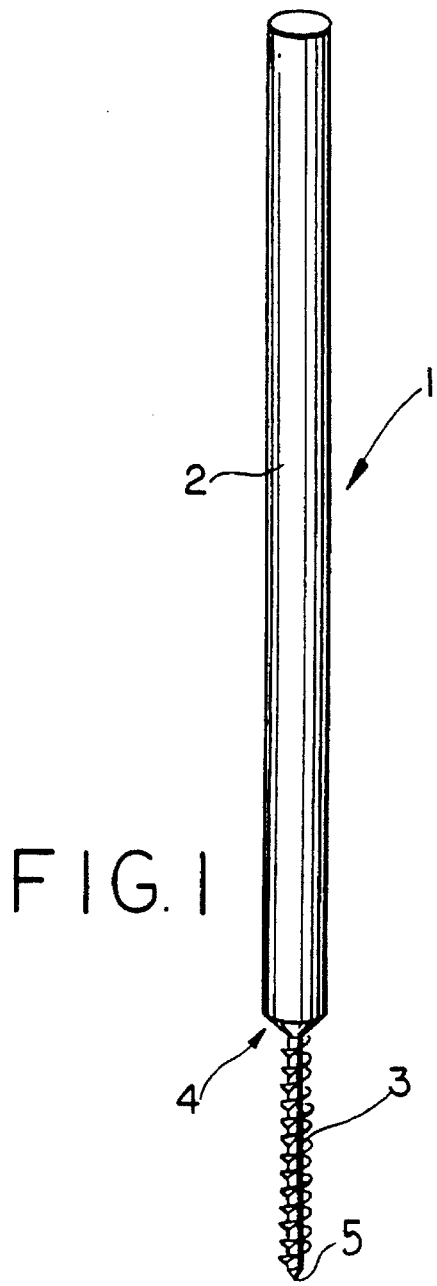
FIG. 1 is an enlarged view in elevation of a small-bone pin or compression wire of the invention.

In FIG. 1, a small-bone fixation pin or compression wire 1 is seen to comprise essentially a smooth-walled shank portion 2, with an adjoining distal threaded portion 3. The outside diameter of the threaded portion 3 is smaller than the outside diameter of the shank portion 2; the diameter of the threaded portion is preferably constant, except for a sharp distal end 5, for self-tapping entry into bone tissue. Between the threaded portion 3 and the shank portion 2, as seen in FIG. 2, a frusto-conical shoulder or step 2 serves as an abutment for a bone fragment A which is to be fixed onto the remainder of the main bone B, by advancing the threaded portion 3 into the main bone.

The half-angle of conical shoulder convergence, i.e., with respect to the central axis of pin 1, is suitably in the range 30° to 60°, and is preferably about 45°.

Figure 2:
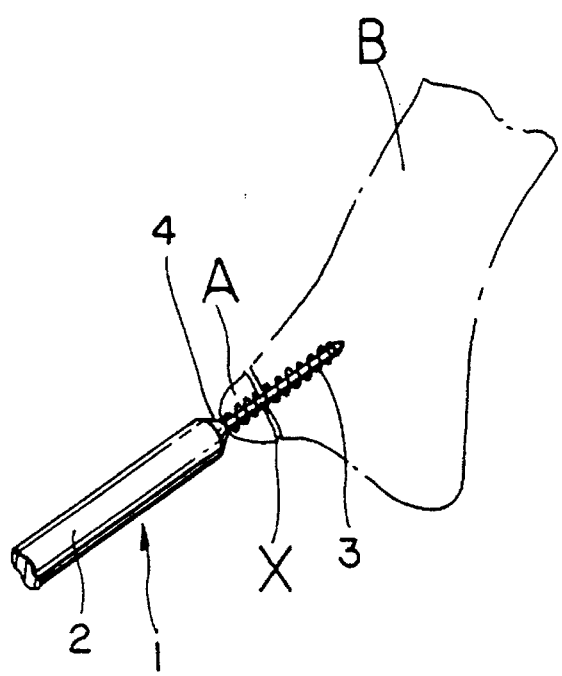
FIG. 2 is a simplified section, on a reduced scale, through a small bone, fractured at X, to show use of the invention.

Alternatively, and as shown in FIG. 3, a compression wire or pin may have a substantially radial shoulder 4' between its smooth shank 2 (diameter $D_1$), adapted for drill-chucked drive, and its reduced self-tapping threaded end 3 (of diameter $D_2$), in which case, a fixation as in FIG. 2 will be understood to use the radial shoulder 4' for larger-area contact with the fragment A to retain a predetermined retaining force of fragment A against the remainder B of the same bone. FIG. 3 further serves to identify overall length $L_1$ and threaded length $L_2$, as well as to indicate at α, the ground angle of convergence of the self-tapping distal end of threaded portion 3; the angle α is suitably about 45 degrees.

To obtain an idea of the sizes involved, it is pointed out that a fixation pin 1, may for example, have a length of 100-mm, with the threaded portion 3 having a length of 15-mm and the shank portion 2 a length of 85-mm. The diameter of the threaded portion can be 1.4 to 1.6-mm when, for example, the diameter of the shank portion 2 is 2-mm.

More specifically, and by way of example, a fixation pin 1 should be of such overall length ($L_1$) as to permit well-chucked engagement to the shank portion 2, with a generous allowance of exposed shank, for unobstructed viewing by the surgeon; this can be taken to mean at least a viewable 25-mm length of shank to the shoulder region 4, when chucked to a portable drill. And to provide the surgeon with a range of fixation pins sufficient for the wide variety of small-bone fractures encountered in practice, it is currently preferred to provide sets or kits of such pins, in three standardized shank diameters, namely 1.5-mm, 2.0-mm and 3-mm diameter respectively, and to provide all pins to the same overall length ($L_1$) of at least 100-mm and preferably 120-mm. In general, it is considered suitable to provide the outer diameter $D_2$ of all threaded ends 3 at a 70 to 80 percent relationship to the shank diameter, and to provide progressively stepped increments of thread length ($L_2$) in a full assortment that is preferred for each shank diameter. Thus, for a small 1.5-mm diameter shank-size assortment, thread length ($L_2$) is selectable from a preferred group of eight pins, ranging in 2-mm increments from 7-mm to 21-mm, wherein all threads are of 1.2-mm diameter, all to serve for fixation of the smallest fragments in small bones. Thus also, for a large 3-mm diameter shank-size assortment, thread length ($L_2$) is selectable from another preferred group of eight pins, ranging in 5-mm increments from 20-mm to 55-mm, wherein all threads are of 2.2-mm diameter, all to serve for fixation of larger fragments in relatively large bones. The intermediate or 2-mm diameter shank assortment is currently preferred to serve intermediate situations, wherein thread length is in small (e.g. 2-mm) increments in a range 11-mm to 25-mm, and in larger (e.g. 5-mm) increments for greater threaded lengths, all with 1.6-mm thread diameter.

With the indicated orders of dimensional magnitude, and after a selected pin has been driven to fix a bone fragment, the shank portion 2 can easily be cut off by suitable nippers so that protruding regions of the threaded portion or of the shank portion can easily be removed.

Depending upon the externally exposed shape or condition of a particular bone fragment to be secured to the remainder of the same bone, the invention is shown in FIG. 4 to permit optional employment of a washer 6, which, as in the case of all or any pins of the invention, is also preferably and suitably of stainless steel. In FIG. 5, diametric dimensions $D_1$ and $D_2$ identify the sizes and size relationships discussed above for the shank and threaded portions (2, 3) of the pin of FIG. 3, namely, with a radial shoulder 4' between shank 2 and the threaded end 3.

Washer 6 is flat and features a bore of diameter $D_3$ to clear the threads of portion 3 and a conical counterbore or chamfer at both ends of the bore. The outer diameter $D_4$ of the washer may suitably be 1.5 to 2.5 times the shank diameter $D_1$. The inner diameter of the chamfer is the bore diameter $D_3$, which is less than the shank diameter $D_1$; and the outer diameter $D_5$ of the chamfer exceeds the shank diameter $D_1$, to an extent which is at least as great at the radial clearance between the washer bore and the thread diameter $D_2$. In these circumstances, the driven fit of shoulder 4' to washer 6, with washer 6 compressing bone fragment A to bone remainder B, may be a perfectly centered engagement of the circular rim of shoulder 4' to the adjacent chamfer, as shown; and it is also possible for washer 6 to be slightly angled (i.e., tilted) in self-adaption to a local profile or other feature at washer contact with fragment A, in which case, shoulder 4' engagement to the adjacent chamfer of the washer will be at only slight departure from the circle-to-cone engagement for the perfectly centered situation. In any event, the slight tilting of washer 6 with respect to a normal to the central axis of the pin will in no sense impair a shank-driven washer compression of bone fragment A to bone remainder B.

In FIG. 5, the same washer 6, with like preferably 45-degree chamfers at opposite ends of its bore, is shown in combination with a pin as in FIGS. 1 and 2, namely with a conical transition 4 between shank and threaded ends of the pin. The involved cone-to-cone engagement is self-centering, and washer is urged to assume an orientation perpendicular to the pin axis when shank 2 is driven to apply fragment-fixation compression over the area of the fracture X.

In FIG. 6, washer 6' has a distal face 7 that is concave, being suitably a circular or parabolic arc of revolution about the axis of the bone pin. The axial depth d of the concavity 7 may be about one-third of the axial extent of washer 6'. The small-bone fragment A is of course enlarged but is seen to present a concave shape for washer (6') engagement with the convex shape of the bone fragment, in close conformance with the concave depth and curvature of the distal face 7 of the washer. This is as it should be for the fracture X as shown in FIG. 6, wherein bone-engagement via distal face 7 provides an enlarged area of bone-fragment support and compression surrounding the region of threaded-portion (3) engagement to bone at A and at B.

It is realized, however, that not all bone fragments will present a convex shape that is so well accommodated by the distal face 7 that has been described. To best equip the orthopedic surgeon who must deal with whatever confronts him, the invention is to be understood as being available in kit form, wherein at least one and preferably several washers 6 are provided for each bone screw, pin, or wire 1, and wherein the several washers 6 differ as to axial depth d of the concavity 7. The surgeon has further opportunity to adapt the described washer 6 to particular circumstances of small bone fragment contour, in that the washer 6 may be bent as necessary by pliers or other tools which are standard equipment for the orthopedic surgeon. Thus, if need be, a washer 6', of preselected axial depth d of its otherwise spherical distal face 7 may be bent to distort the distal face 7 into a more complex curvature wherein the curvature is, for example, (i) of relatively short-focus parabolic nature in a first longitudinal section which includes the pin axis and (ii) of longer-focus parabolic nature in a second longitudinal section, taken 90 degrees from the first longitudinal plane.

A kit of the nature indicated preferably includes a set of small-bone pins or compression wires 1, wherein there is at least one pin or wire 1 of each of several shank (2) diameters, illustratively of 3-mm, 2-mm, and/or 1.5-mm diameter, with thread (3) diameters of 2.2-mm, 1.6-mm, and/or 1.2-mm, respectively, in ranges of incrementally stepped thread lengths, as noted above for each of the respective thread lengths. Such a kit would also include washers 6 (and/or 6') at least to fit the 3-mm and 2-mm shank sizes indicated, and with at least two different axial depths d for each of these shank sizes. In the case of the 3-mm shank size, washers 6 are suitably of 6-mm or 4-mm diameter $D_4$; and in the case of the 2-mm or 1.5-mm shank size, washers 6 are suitably of 3-mm or 4-mm diameter $D_4$.

Each compression wire of the invention provides sufficient length of smooth-walled shank to enable chucked engagement to a standard portable drill, preferably of so-called "cordless" variety. Procedurally, each wire can be installed in a single driven self-tapping operation with entry into both the small bone fragment and the larger remainder of the same bone, from which the small fragment was broken. The wire is set, upon driven rotational entry into the bone, to the extent of shoulder compression of the fragment A to the anchored remainder B of the same bone. In the course of driving the pin through the fractured bone, reduction is maintained by pressure applied to the fragment; and the shoulder keeps the bone fragment from back-sliding when the shoulder reaches the cortex of the fragment. After wire-threading (pin-threading) purposes have been served, the shank portion is no longer necessary and can be readily severed from the installed remainder, using a conventional wire-snip tool, as closely offset as possible from the shoulder 4 (4') region, which is relied upon to retain the fixation of fragment A to remainder B.

FIGS. 7A to 9B provide illustration of a variety of uses of the invention, which in all cases not only simplifies and shortcuts the process and time required for fragment fixation, but also enables greatly enhanced and assured durability of the fixated product, i.e., with compression-wire implantation.

Figure 7A:
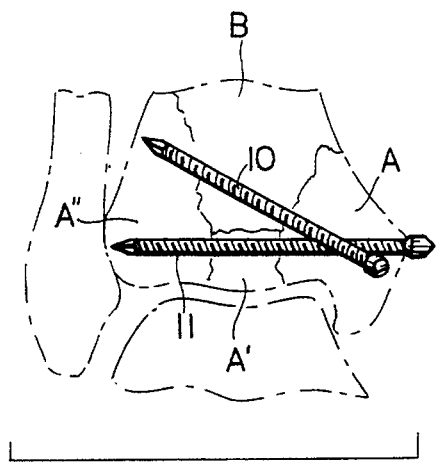
FIG. 7A is a diagram in the nature of FIG. 2, and simplified from an x-ray photograph, to show use of multiple implanted compression wires of relatively large diameter, in the fixation of a comminuted pilon tibial fracture.
Figure 7B:
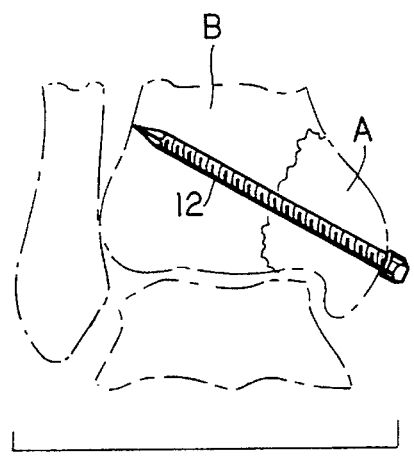
FIG. 7B is a simplified diagram as in FIG. 7A to show the same compression-wire size in the fixation of a medial malleolar fracture.

In FIG. 7A, two large compression-wire implants 10, 11, e.g. 3-mm wire size, are shown with shanks cut off after self-tapping thread advance to the point of shoulder-driven fragment engagements to other fragments A', A" and to the tibial remainder B, in the case of a tibial pilon fracture. And in FIG. 7B, a single compression-wire implant 12 of the same large wire size, is seen to be retaining a fragment A to bone remainder B in reduction of a medial malleolar fracture.

Figure 8A:
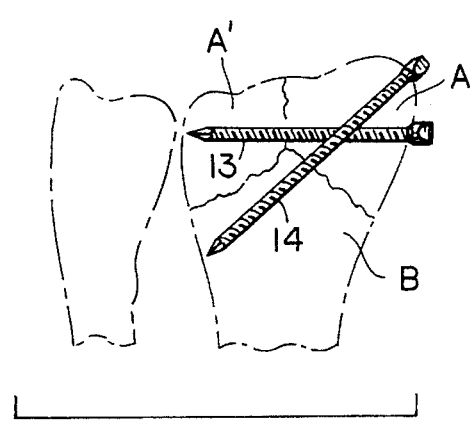
FIG. 8A is a diagram as in FIG. 7A, to show use of multiple compression wires, of medium-size wire, in the fixation of a distal-radius fracture.
Figure 8B:
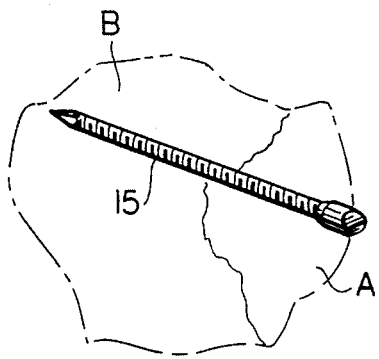
FIG. 8B is a diagram as in FIG. 7B, to show use of a single medium-size compression wire, in the fixation of a proximal radial fracture.

In FIG. 8A, first and second medium-size compression-wire implants 13, 14, e.g. 2-mm wire size, with shanks cut off after implantation, are shown retaining an outer fragment A to remainder bone B and to another fragment A', for the case of an intra-articular distal radius fracture. And in FIG. 8B, a single compression-wire implant 15 of the same medium-size wire, is seen to be retaining a fragment A to remainder bone B in reduction of a proximal radius fracture.

Figure 9A:
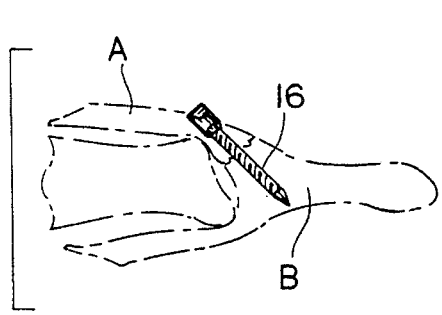
FIG. 9A is a similar diagram, to show use of a small-size compression-wire implant, in the fixation of a mallet-finger fracture.
Figure 9B:
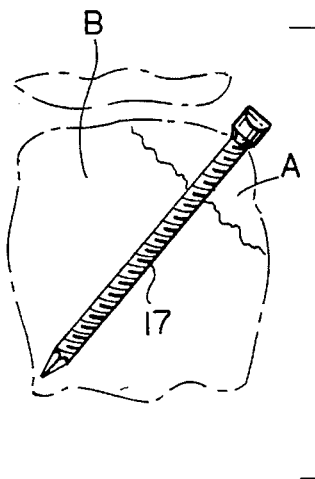
FIG. 9B is another diagram for use of a small-size compression-wire implant, in the fixation of an intra-articular phalangeal fracture.

In FIG. 9A, a single small and short compression-wire implant 16, e.g. 1.5-mm wire size, with shank cut off after implantation, is shown retaining a mallet finger A to remainder bone B. And in FIG. 9B, a single, relatively elongate compression wire 17 of small-wire size is shown fixing a fragment A to remainder bone B, in reduction of an intra-articular phalangeal fracture.

I claim:

1. The method of fixating a fractured bone fragment to adjacent remainder structure of the bone from which the fragment has been fractured, said method comprising the steps of:

(a) selecting a compression wire having an elongate proximal shank of uniform diameter in the range 1-mm to 3-mm, and having a self-tapping distally extending threaded portion of lesser diameter than the shank, said wire having an annular shoulder formation at juncture of said shank to said threaded portion;

(b) selecting a rotary drill and chucking the wire shank to the drill, thereby distally projecting the self-tapping threaded portion;

(c) applying the self-tapping distal end of the wire to exposed cortex of the fragment while positioning the fragment against said remainder structure of the bone, and operating the drill to tap and advance the threaded portion through the fragment and into implanted anchoring engagement with said remainder structure until the shoulder formation engages the fragment to retain the fragment against said remainder structure; and (d) unchucking the drill from the wire.

2. The method of claim 1, including the additional step of cutting off a predetermined proximal length of the shank, after wire-thread implantation and short of said shoulder formation.

3. The method of claim 2, and the further step of removing the wire from implantation in the bone after a period of fracture healing, the removal being by engaging an extractor tool to the portion of wire shank adjacent but external to cortex tissue, and using the extractor tool to unthread the wire from the bone.

4. The method of fixating a fractured bone fragment to adjacent remainder structure of the bone from which the fragment has been fractured, said method comprising the steps of:

(a) selecting a compression wire having an elongate proximal shank of uniform diameter in the range 1-mm to 3-mm, and having a self-tapping distally extending threaded portion of lesser diameter than the shank, said wire having an annular shoulder formation at juncture of said shank to said threaded portion;

(b) selecting an annular washer having a bore of diameter less than said shank diameter and greater than the diameter of said threaded portion; said washer having an outer diameter which is greater than the shank diameter; and assembling the washer to the self-tapping distal end of the wire;

(c) selecting a rotary drill and chucking the wire shank to the drill, thereby distally projecting the self-tapping threaded portion;

(d) applying the self-tapping distal end of the wire to exposed cortex of the fragment while positioning the fragment against said remainder structure of the bone, and operating the drill to tap and advance the threaded portion through the fragment and into implanted anchoring engagement with said remainder structure until the shoulder formation compressionally urges the fragment to retain the fragment against said remainder structure; and (e) unchucking the drill from the wire.

5. The method of claim 4, including the additional step (f) of cutting off a predetermined proximal length of the shank, short of said shoulder formation.

6. The method of claim 4, wherein the step of selecting a compression wire includes selecting a compression wire wherein the shoulder is frusto-conically convergent in the distal direction, and wherein the selected washer has a frusto-conical chamfer compatible for engagement to said shoulder.

7. The method of claim 6, wherein the step of selecting a washer includes selecting a washer that is flat and wherein said chamfer is one of two, respectively at opposite ends of the bore of the washer.

8. The method of fixating a fractured bone fragment to adjacent remainder structure of the bone from which the fragment has been fractured, said method comprising the steps of:

(a) using an x-ray view of the fractured bone, taken at a viewing-axis orientation substantially normal to a prospective alignment axis of bone-screw orientation, to make a determination of threaded-section length to be implanted for purposes of holding the fragment to adjacent structure of the bone from which the fragment was fractured;

(b) selecting a compression wire having an elongate proximal shank of uniform diameter in the range 1-mm to 3 mm, and having a self-tapping distally extending threaded portion of lesser diameter than the shank and of length which substantially accords with the determined screw-length, said wire having an annular shoulder at juncture of said shank to said threaded portion, (c) selecting a rotary drill and chucking the wire shank to the drill, thereby distally projecting the self-tapping threaded portion;

(d) applying the self-tapping distal end of the wire to exposed cortex of the fragment while positioning the fragment against said remainder structure of the bone, and operating the drill to tap and advance the threaded portion on said alignment axis and through the fragment and into implanted anchoring engagement with said remainder structure until the shoulder formation engages the fragment to retain the fragment against said remainder structure; and (e) unchucking the drill from the wire.

9. The method of claim 8, including the additional step of cutting off a proximal portion of the length of the shank, after wire-thread implantation and short of said shoulder.

10. The method of fixating a fractured bone fragment to adjacent remainder structure of the bone from which the fragment has been fractured, said method comprising the steps of:

(a) selecting a compression wire having an elongate proximal shank of uniform diameter in the range 1-mm to 3-mm, and having a self-tapping distally extending threaded portion of lesser diameter than the shank, said wire having an annular shoulder formation at juncture of said shank to said threaded portion, and said threaded portion having a cutting distal-tip end which is characterized by plural angularly spaced ground surfaces which converge distally from distal threads of said threaded portion;

(b) selecting a rotary drill and chucking the wire shank to the drill, thereby distally projecting the self-tapping threaded portion;

(c) applying the self-tapping distal-tip end of the wire to exposed cortex of the fragment while positioning the fragment against said remainder structure of the bone, and operating the drill to tap and advance the threaded portion through the fragment and into implanted anchoring engagement with said remainder structure until the shoulder formation engages the fragment to retain the fragment against said remainder structure; and (d) unchucking the drill from the wire.

* * * * *